United States Patent [19]

Groth et al.

[11] Patent Number: 5,684,163
[45] Date of Patent: Nov. 4, 1997

[54] PROCESS FOR THE PREPARATION OF N-(ORTHO-ALKYLPHENYL)-IMIDES

[75] Inventors: Torsten Groth, Köln; Bernd-Michael König, Bergisch Gladbach; Josef Käsbauer, Wermelskirchen; Michael Schwamborn, Köln, all of Germany

[73] Assignee: Bayer Aktiengesellschaft, Leverkusen, Germany

[21] Appl. No.: 595,463

[22] Filed: Feb. 5, 1996

[30] Foreign Application Priority Data

Feb. 13, 1995 [DE] Germany .................. 195 04 626.9

[51] Int. Cl.⁶ .................. C07D 207/452; C07D 207/456; C07D 207/40
[52] U.S. Cl. .................. 548/549; 548/544; 548/545; 548/546; 548/548
[58] Field of Search ................................. 548/549

[56] References Cited

U.S. PATENT DOCUMENTS

| | | | |
|---|---|---|---|
| 3,890,270 | 6/1975 | Minieri | 260/45.8 N |
| 4,904,803 | 2/1990 | Fujita et al. | 548/548 |
| 5,136,052 | 8/1992 | Van Gysel et al. | 548/549 |

FOREIGN PATENT DOCUMENTS

| | | |
|---|---|---|
| 0165574 | 12/1985 | European Pat. Off. . |
| 0177031 | 4/1986 | European Pat. Off. . |
| 0461096 | 12/1991 | European Pat. Off. . |
| 2100800 | 7/1971 | Germany . |
| 1041027 | 9/1966 | United Kingdom . |

OTHER PUBLICATIONS

Patent Abstracts of Japan, vol. 17, No. 361, abstract of JP 05–051362, (1983).
Chemical Abstracts, vol. 75, abstract No. 118127y, p. 203, abstract of DE 2,100,800, (1971).

*Primary Examiner*—David B. Springer
*Attorney, Agent, or Firm*—Sprung Horn Kramer & Wood

[57] ABSTRACT

A process for the preparation of a N-)ortho-alkylphenyl)-imide of the formula

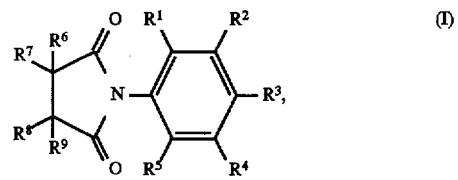

in which $R^1$ to $R^9$ is defined in the specification which comprises reacting a cyclic anhydride of the formula

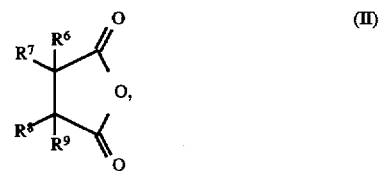

wherein $R^6$ to $R^9$ are difined in the specification with an amine of the formula

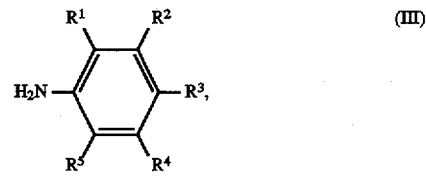

optionally in the presence of an acid catalyst and optionally in the presence of a solvent which is immiscible or only slightly miscible with water but can form an azeotrope with water, at a temperature between 100° to 200° C. under conditions so that the water formed during the reaction is removed from the reaction mixture without the addition of a polymerization inhibitor or a dipolar solvent. The final products are used as intermediates to prepare heat-stable plastics as well as intermediates to prepare pharmaceutical and agricultural chemicals.

13 Claims, No Drawings

PROCESS FOR THE PREPARATION OF N-(ORTHO-ALKYLPHENYL)-IMIDES

BACKGROUND OF THE INVENTION

The present invention relates to a particularly advantageous process for the preparation of N-(ortho-alkylphenyl)-imides which can be used for the preparation of heat-stable plastics and as intermediate products for pharmaceuticals and plant protection agents.

It is known to prepare N-(ortho-alkylphenyl)-maleimides by reaction of correspondingly substituted anilines with maleic acid anhydride (MAA) and cyclization of the resulting N-substituted maleamic acids with condensing agents, for example acetic anhydride (see, for example, U.S. Pat. No. 3,890,270). However, the use of condensing agents is uneconomical and leads to by-products which have to be separated off in a complicated manner and disposed of or recycled. Furthermore, working up is carried out by addition of water, which leads to organically polluted waste waters which have to be disposed of in an expensive manner.

It is furthermore known to prepare N-phenylmaleimide (NPMI) by reaction of MAA with aniline at elevated temperature in the presence of an acid catalyst and an inert solvent which is immiscible or only slightly miscible with water but forms azeotropes with water, the water formed being removed from the circulation. The yields are then high to a certain extent only if the reaction is carried out in the presence of polymerization inhibitors (see, for example, EP-A 165 574) and dipolar aprotic solvents, for example dimethylformamide (see, for example, EP-A 177 031) or recycled NPMI (see, for example, EP-A 461 096). Such additional measures mean an advance in the preparation of NPMI, but they are also associated with disadvantages regarding process technology and economic disadvantages, since the additives cause increased expenditure for their disposal or recycling. Furthermore, here also working up is in general carried out by addition of water, which leads to the abovementioned additional disadvantages.

Finally, it is known from DB-A 21 00 800 that N-(ortho-alkylphenyl)-maleimides can be prepared by reaction of the correspondingly substituted anilines with MAA in the presence of bases, for example triethylamine. However, this process chiefly gives insoluble polymeric products (see present Example 10).

There is therefore still the need for a process for the preparation of N-(ortho-alkylphenyl)-imides in which the disadvantages described are avoided and products can be obtained in a manner which is simple in terms of process technology with yields of more than 90% of theory and in purities of more than 95%.

SUMMARY OF THE INVENTION

A process has now been found for the preparation of N-(ortho-alkylphenyl)-imides of the formula

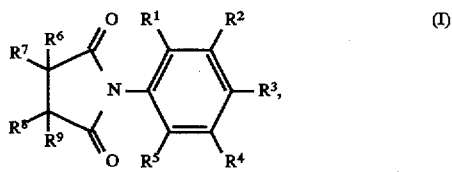

in which
$R^1$ represents a $C_1$–$C_6$-alkyl radical and
$R^2$ to $R^9$ independently of one another in each case represent hydrogen, optionally substituted $C_1$–$C_6$-alkyl, optionally substituted $C_2$–$C_6$-alkenyl, halogen, $NO_2$, CN and/or $C_1$–$C_6$-alkoxy, wherein $R^6$ and $R^7$ also together can represent $R^{10}$—CH=, where $R^{10}$ =hydrogen or $C_1$–$C_4$-alkyl, or
$R^7$ and $R^8$ also together can represent a covalent bond, in which a cyclic acid anhydride of the formula

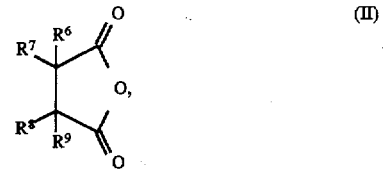

in which
$R^6$ to $R^9$ have the meaning given in the case of formula (I), is reacted with an amine of the formula

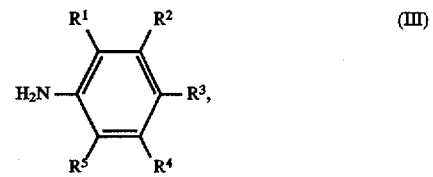

in which
$R^1$ to $R^5$ have the meaning given in the case of formula (I), which is characterized in that the water of reaction is removed from the circulation at 100° to 200° C. without the addition of polymerization inhibitors and without the addition of dipolar aprotic solvents.

DETAILED DESCRIPTION OF THE INVENTION

If $R^2$ to $R^9$ represent substituted alkyl or alkenyl radicals, possible substituents are, for example, halogen, $NO_2$, CN and/or $C_1$–$C_6$-alkoxy. Halogen in the definition of $R^2$ to $R^9$ and as a substituent for alkyl and alkenyl radicals represents, for example, fluorine, chlorine, bromine and/or iodine, preferably fluorine, chlorine and/or bromine.

In the formulae (I) and (III), $R^1$ preferably represents $C_1$–$C_4$-alkyl and $R^2$ to $R^5$ independently of one another preferably represent hydrogen, unsubstituted straight-chain or branched $C_1$–$C_4$-alkyl, unsubstituted straight-chain or branched $C_2$–$C_4$-alkenyl, chlorine, $NO_2$, CN and/or $C_1$–$C_6$-alkoxy.

In the formulae (I) and (II), $R^6$ to $R^9$ independently of one another preferably represent hydrogen, unsubstituted straight-chain or branched $C_1$–$C_4$-alkyl and/or unsubstituted straight-chain or branched $C_2$–$C_4$-alkenyl, or $R^6$ and $R^7$ together represent $R^{10}$—CH=, where $R^{10}$=hydrogen, methyl or ethyl, and $R^8$ and $R^9$ independently of one another represent hydrogen, methyl, ethyl and/or chlorine, or $R^7$ and $R^8$ together represent a covalent bond and $R^6$ and $R^9$ independently of one another represent hydrogen, methyl, ethyl and/or chlorine.

Cyclic acid anhydrides of the formula (II) which are particularly preferably employed are maleic acid anhydride, itaconic acid arthydride and monochloromaleic acid anhydride.

Amines of the formula (III) which are particularly preferably employed are o-toluidine, 2,3-, 2,4-, 2,5- and 2,6-dimethylaniline, 2,6-diethylaniline, 2-ethyl-6-methylaniline, 2-isopropylaniline, 2-chloroaniline and 2,6-diisopropylaniline.

The following N-(ortho-alkylphenyl)-imides of the formula (I) are particularly preferably prepared: N-(2- methylphenyl)-maleimide, N-(2-ethyl-6-methylphenyl)-maleimide, N-(2,6-dimethylphenyl)-maleimide, N-(2,6-diethylphenyl)-maleimide, N-(2,6-diisopropylphenyl)-maleimide, N-(2-isopropylphenyl)-maleimide and the corresponding monochloromaleimides and itaconimides.

If appropriate, the reaction according to the invention can be carried out in the presence of acid catalysts. Possible acid catalysts are, for example, the most diverse organic and inorganic proton acids as well as acid ion exchangers. Preferred acids are sulphuric acid, phosphoric acid, alkylsulphonic acids, such as methanesulphoric acid, arylsulphonic acids, such as benzenesulphonic acid, toluenesulphonic acids and xylenesulphonic acids, and strongly and weakly acid ion exchangers in the H form. Acid catalysts can be employed, for example, in amounts of 0 to 10% by weight, based on the acid anhydride of the formula (II). This amount is preferably 0.1 to 10% by weight, in particular 0.5 to 8% by weight.

If appropriate, the reaction according to the invention can be carried out in the presence of solvents which are immiscible or only slightly miscible with water but can form azeotropes with water. Such solvents are, for example, toluene, xylenes, cumene, mesitylene, Tetratin, Decalin, chlorobenzene, dichlorobenzenes, ethylbenzene, anisole, tetrahydrodicyclopentadiene and any desired mixtures of these solvents. The solvents can serve to remove the water of reaction formed in the reaction according to the invention from the circulation by azeotropic distillation from the reaction mixture. By varying the solvent and/or the pressure, the temperature at which the water is removed azeotropically can be varied. If solvents are employed, this can be done, for example, in amounts of up to 70% by weight, based on the reaction mixture (including solvents). It is also possible to use relatively little solvent or no solvent at all, for example 0 to 20% by weight of solvent, based on the reaction mixture (including solvent, if present).

The molar ratio of cyclic acid anhydride of the formula (II) to amine of the formula (III) can be, for example, 0.5:1 to 1.5:1. Equimolar amounts or a slight excess of cyclic acid anhydride is preferably used, for example up to 1.1 mol of cyclic acid anhydride per mole of amine.

It is advantageous to initially introduce the cyclic acid anhydride of the formula (II), if appropriate together with the acid catalyst and if appropriate together with the solvent, into the reaction vessel and to meter in the amine of the formula (III). The corresponding amide acid initially forms from the cyclic acid anhydride and the amine, and is in general rapidly converted into the corresponding N-substituted imide of the formula (I) with water being split off.

The reaction temperature in the process according to the invention is preferably in the range from 110° to 190° C. The pressure is not critical. The reaction can be carried out under increased, reduced or normal pressure. It is preferably carded out under normal pressure.

The water of reaction can be removed from the circulation not only with the aid of a suitable solvent, as described above, but also by direct removal from the reaction mixture by distillation or by blowing out with a stream of inert gas.

The reaction mixture present after the reaction according to the invention and after the water of reaction has been removed from the circulation can be worked up, for example, by distillation, i.e. the N-(ortho-alkylphenyl)-imide of the formula (I) prepared can be isolated by distillation, preferably under reduced pressure.

If a solvent has been added, it is expedient to separate off the solvent before isolating the imide, for example by stripping off in vacuo or distilling under normal or moderately reduced pressure. The solvent which has been separated off can be re-used. The imide which remains may already be sufficiently pure, especially if deacidification (see below) has been carried out beforehand.

It is advantageous to separate off by-products which give an acid reaction, excess cyclic anhydride and/or acid catalysts by deacidification before the imide prepared is isolated. For this, a non-aqueous base can be added to the solvent-containing or solvent-free reaction mixture and the precipitate which forms can be filtered off. Suitable bases are, for example, ammonium, alkali metal and/or alkaline earth metal carbonates, urea, ammonium carbonates and/or anhydrous ammonia. The absence of water does not have to be absolute. The products available commercially as anhydrous quality are in general sufficiently anhydrous. It is advantageous to maintain temperatures of, for example, 10° to 100° C., preferably 20° to 80° C., during and/or after addition of the non-aqueous base. If appropriate, the precipitate which has been separated off can be washed and the wash liquid can then be worked up together with the filtrate. The solvents mentioned above are particularly suitable, for example, for washing the precipitate.

Non-aqueous bases can be employed, for example, in amounts of 0 to 150 mol %, based on the acid components to be separated off. This amount is preferably 50 to 130 mol %.

Finally, the N-(ortho-alkylphenyl)-imide of the formula (I) isolated can be made up in any desired manner. For example, it can be converted into the form of flakes, pastilles, granules or a solution, for example in styrene or acrylonitrile.

The process according to the invention has a number of advantages. Thus, it requires no dipolar aprotic cosolvents, a polymerization inhibitor can be dispensed with during the reaction, the work is carried out in a largely anhydrous medium and, especially if the procedure uses small amounts of solvent or is solvent-free, high space/time yields are achieved.

It is particularly surprising that N-(ortho-alkylphenyl)-imides of the formula (I) can be prepared in the manner according to the invention in such a simple way with high yields and purifies. Because of the steric hindrance by the radical $R^1$, a lower reactivity and therefore an increased tendency to undergo side reactions was to be expected with the amines of the formula (III) to be employed. The technical development in the field of the preparation of N-phenyl-imides to date has recently led to relatively complicated processes. The relatively simple process according to the invention was therefore not obvious.

EXAMPLES

Example 1

500 g of a xylene isomer mixture, 206.0 g of maleic acid ahnydride and 5.0 g of sulphuric acid. (80% strength) were stirred under reflux (142° C.) using a water separator. After 10 minutes, 2 ml of water had been removed from the circulation and a clear solution had formed. 270.4 g of 2-ethyl-6-methylaniline were metered in under the surface under a blanket of nitrogen at 142° to 150° C. in the course of 4 hours and 38 ml of water were removed from the circulation azeotropically. The solution was subsequently stirred for 1 hour, a further 2 ml of water were removed from the circulation, the mixture was then cooled to 60° C., 11.0 g of solid ammonium carbonate were added, the mixture was stirred for 1 hour and filtered over a pressure suction filter and the pale yellow filtrate was evaporated on a rotary evaporator under 22 mbar (bath temperature: 99° C.). After addition of 122 mg of a polymerization inhibitor (Vulkanox® ZKF) and 350 mg of phosphoric acid (85% strength), the residue (425 g) was distilled in vacuo over a 10 cm Vigreux column (overhead temperature: 125° to 131° C., bottom temperature: 146° to 148° C., pressure: 1 mbar). 409 g of N-(2-ethyl-6-methylphenyl)-maleimide (95% of theory) with a content of 99.8% by weight (determined by HPLC), a melting point of 85° C. and an acid number of less than 0.1 mg of potassium hydroxide/g were obtained.

Examples 2 to 5

The procedure was as in Example 1, but other amines were employed and other N-(ortho-alkylphenyl)-maleimides were obtained. Details can be seen from the following table.

| Ex. no. | Amine employed | N-(ortho-Alkylphenyl)-maleimide obtained | Yield (% of theory) | Melting point (°C.) |
|---|---|---|---|---|
| 2 | o-Toluidine | N-(2-Methylphenyl)-maleimide | 93 | 72–72.5 |
| 3 | 2,6-Diethyl-aniline | N-(2,6-Diethylphenyl)-maleimide | 92 | 73.5–73.8 |
| 4 | 2,6-Dimethyl-aniline | N-(2,6-Dimethyl-phenyl)-maleimide | 92 | 99–100 |
| 5 | 2-Isopropyl-aniline | N-(2-Isopropylphenyl)-maleimide | 91 | 99.2–99.4 |

Example 6

The procedure was as in Example 1, but the final distillation in vacuo was not carried out. The 425 g of residue was N-(2-ethyl-6-methylphenyl)-maleimide in a yield of 96.6% of theory, with a content of 97.8% by weight (determined by HPLC), a melting point of 84.5° to 85° C. and an acid number of less than 0.1 mg of potassium hydroxide/g.

Example 7

The procedure was as in Example 1, but no deacidification with ammonium carbonate was carried out. 410 g of N-(2-ethyl-6-methylphenyl)-maleimide (95% of theory) with a content of 99.5% by weight (determined by HPLC), a melting point of 84.5° to 85° C. and an acid number of 1.3 mg of potassium hydroxide/g were obtained.

Example 8

50 g of toluene, 206.0 g of maleic acid anhydride and 2.0 g of p-toluenesulphonic acid hydrate were initially introduced into the reaction vessel and were heated under reflux (135° C.) using a water separator. 270.4 g of 2-ethyl-6-methylaniline were metered in under the surface under a blanket of nitrogen in the course of 4 hours, during which 36 ml of water were separated off. The boiling point, which rises in the course of the metering, was limited to not more than 152° C. by occasional addition of a total of 50 g of toluene. Thereafter, the solution was subsequently stirred for a further hour, a further 2 ml of water being removed from the circulation, and was then cooled to 65° C., 11.0 g of solid ammonium carbonate were added, the mixture was stirred for a further hour and filtered over a pressure suction filter and the pale yellow filtrate was evaporated on a rotary evaporator under 22 mbar (bath temperature: 99° C.). After addition of 122 mg of a polymerization inhibitor (Vulkanox® ZKF) and 350 mg of phosphoric acid (85% strength), the residue (416 g) was distilled in vacuo over a 10 cm Vigreux column. The distillation conditions were as stated in Example 1. 396 g of N-(2-ethyl-6-methylphenyl)-maleimide (91.7% of theory) with a content of 99.7% by weight (determined by HPLC), a melting point of 85° C. and an acid number of less than 0.1 mg of potassium hydroxide/g were obtained.

Example 9 (comparison example according to U.S. Pat. No. 3,890,270)

196 g of maleic acid arthydride were dissolved in 2.5 l of diisopropyl ether at room temperature. A solution of 270.4 g of 2-ethyl-6-methyl-aniline in 200 ml of diisopropyl ether was added dropwise at room temperature in the course of 4 hours, the resulting suspension was cooled to 15° to 20° C. and the solid was filtered off with suction and introduced into a mixture of 670 ml of acetic arthydride and 65 g of anhydrous sodium acetate. The suspension formed was heated to 100° C., while stirring, stirred at this temperature for 30 minutes, subsequently cooled to 30° C. and introduced into 1.3 l of ice-water. The precipitate was filtered off with suction, washed with ice-water and petroleum ether and dried. 321 g of N-(2-ethyl-6-methylphenyl)-maleimide (92.9% of theory) with a content of 97.8% by weight (determined by HPLC) and a melting point of 84.5° to 85° C. were obtained.

Example 10 (comparison example according to DE-A 21 00 800)

500 g of a xylene isomer mixture, 196 g of maleic anhydride and 0.60 g of tri-ethylamine were stirred under reflux using a water separator, and 240.4 g of 2-ethyl-6-methylaniline were added under a nitrogen blanket in the course of 4 hours. The solution initially became brown in colour and then deep red, and large quantities of a solid separated out, making stirring very difficult. 24 ml of water were removed from the circulation. After cooling, the solidified reaction mixture (about 900 g) was analysed. It contained only 4.4% by weight of N-(2-ethyl-6-methylphenyl)-maleimide. The yield was thus only 9.2% of theory.

What is claimed is:

1. A process for the preparation of a N-(ortho-alkylphenyl)-imide of the formula

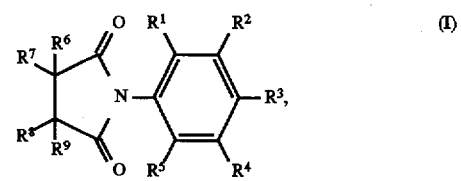

in which

R$^1$ represents a C$_1$–C$_6$-alkyl radical and

R$^2$ to R$^9$ independently of each other represents hydrogen; optionally substituted C$_1$–C$_6$-alkyl wherein the substituents are selected from the group consisting of halogen, NO$_2$, CN, and C$_1$–C$_6$-alkoxy;

optionally substituted C$_2$–C$_6$-alkenyl wherein the substituents are selected from the group consisting of halogen, NO$_2$, CN, and C$_1$–C$_6$-alkoxy, halogen; NO$_2$; CN, or C$_1$–C$_6$-alkoxy, wherein R$^6$ and R$^7$ optionally together can form R$^{10}$—C=, wherein R$^{10}$ is hydrogen or C$_1$–C$_4$-alkyl or R$^7$ and R$^8$ optionally together can form a double bond, which comprises reacting a cyclic anhydride of the formula

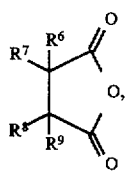
(II)

wherein $R^6$ to $R^9$ are defined above with an amine of the formula

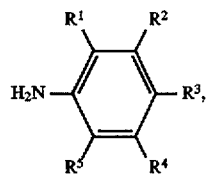
(III)

wherein $R^1$ and $R^5$ have the meaning given in the case of formula (I), optionally in the presence of an acid catalyst and optionally in the presence of a solvent which is immiscible or only slightly miscible with water but can form an azeotrope with water, at a temperature between 100° to 200° C. under conditions so that the water formed during the reaction is removed from the reaction mixture without the addition of a polymerization inhibitor or a dipolar solvent.

2. The process according to claim 1, wherein $R^1$ represents $C_1$–$C_4$-alkyl, $R^2$ to $R^5$ independently represents hydrogen, optionally substituted $C_1$–$C_4$-alkyl wherein the substituents are selected from the group consisting of halogen, $NO_2$, CN, and $C_1$–$C_6$-alkoxy; optionally substituted alkenyl wherein the substituents are selected from the group consisting of halogen; $NO_2$, CN, and $C_1$–$C_6$-alkoxy; chlorine, $NO_2$; CN; and $C_1$–$C_6$-alkoxy;

$R^6$ to $R^9$ independently represent hydrogen, optionally substituted straight-chain or branched $C_1$–$C_4$-alkyl wherein the substituents are selected from the group consisting of halogen, $NO_2$, CN and $C_1$–$C_6$-alkoxy; or optionally substituted straight-chain or branched $C_2$–$C_4$-alkenyl wherein the substituents are selected from the group consisting of halogen, $NO_3$, CN and $C_1$–$C_6$-alkoxy;

or $R^6$ and $R^7$ together represent $R^{10}$—CH= wherein $R^{10}$ is hydrogen, methyl or ethyl and $R^8$ and $R^9$ independently represent hydrogen, methyl, ethyl, and chlorine, or $R^7$ and $R^8$ together form a covalent bond and $R^6$ and $R^4$ independently represent hydrogen, methyl, ethyl or chlorine.

3. The process according to claim 1, wherein the cyclic arthydride is selected from the group consisting of maleic acid anhydride, itaconic acid anhydride or monochloromaleic acid anhydride and the amine is selected from the group consisting of o-toluidine, 2,3-, 2,4-, 2,5- or 2,6-dimethylaniline, 2,6-diethylaniline, 2-ethyl-6-methylaniline, 2-isopropylaniline, 2-chloroaniline or 2,6-diisoproylaniline.

4. The process according to claim 1, wherein 0 to 10% based upon the acidic hydride, of the acid catalyst is present.

5. The process according to claim 1, wherein 70% by weight, based upon the reaction mixture of solvent, is present.

6. The process according to claim 1, wherein the molar ratio of the cyclic acid hydride to the amino is 0.5:1 to 1.5:1.

7. The process according to claim 1, wherein the cyclic acid anhydride is first introduced into the reaction vessel optionally together with the acid catalyst and the solvent followed by metering in the amine.

8. The process according to claim 1, wherein the water formed during the reaction is removed by a water separator, by distillation or by using an azeotrope.

9. The process according to claim 1, wherein the water formed during the reaction is removed by blowing out with a stream of inert gas.

10. The process according to claim 1, wherein the resulting product is recovered by distillation.

11. The process according to claim 1, wherein the excess cyclic anhydride or acid catalyst is removed by adding a non-aqueous base before isolating the imide wherein said base is selected from the group consisting of ammonium, alkali metal carbonates, alkaline earth metal carbonates, urea, ammonium carbonates and/or anhydrous ammonia.

12. The process according to claim 11, wherein 0 to 150 mol % of base, based upon the acid components, is employed.

13. The process according to claim 1, wherein N-(2-ethyl-6-methylphenyl)-maleimide is prepared which comprises reacting maleic acid anhydride in the presence of sulphuric acid as the acid catalyst at a temperature of 142° C., removing the water thus formed by means of a water separator and then adding metering in 2-ethyl-6-methylamine under nitrogen and stirring while removing the water thus formed azeotropically.

* * * * *

UNITED STATES PATENT AND TRADEMARK OFFICE
CERTIFICATE OF CORRECTION

PATENT NO. : 5,684,163
DATED : November 4, 1997
INVENTOR(S) : Groth, et al.

It is certified that error appears in the above-indentified patent and that said Letters Patent is hereby corrected as shown below:

Col. 8, line 3    Delete " $R^4$ " and substitute -- $R^8$ --

Col. 8, line 6    Delete " arthydride " and substitute -- anhydride --

Signed and Sealed this

Fourth Day of August, 1998

Attest:

BRUCE LEHMAN

Attesting Officer

Commissioner of Patents and Trademarks